United States Patent [19]
Crotzer

[11] Patent Number: 5,910,700
[45] Date of Patent: Jun. 8, 1999

[54] DUST SENSOR APPARATUS

[76] Inventor: David R. Crotzer, 19 Thorndike St., Nashua, N.H. 03060

[21] Appl. No.: 09/045,458

[22] Filed: Mar. 20, 1998

Related U.S. Application Data

[60] Provisional application No. 60/042,765, Mar. 20, 1997.

[51] Int. Cl.[6] ................................................. H01L 41/08
[52] U.S. Cl. ........................... 310/338; 310/316; 310/366
[58] Field of Search ................................... 310/366, 369, 310/328, 331, 316, 338

[56] References Cited

U.S. PATENT DOCUMENTS

| | | | |
|---|---|---|---|
| 4,431,938 | 2/1984 | Inoue | 310/348 |
| 4,562,725 | 1/1986 | Oka et al. | 73/29 |
| 4,911,801 | 3/1990 | Pons | 204/59 R |
| 4,965,698 | 10/1990 | Thoma et al. | 361/286 |
| 5,089,741 | 2/1992 | Park et al. | 310/332 |
| 5,129,262 | 7/1992 | White et al. | 73/599 |
| 5,212,988 | 5/1993 | White et al. | 73/599 |
| 5,417,100 | 5/1995 | Miller et al. | 73/31.02 |
| 5,478,756 | 12/1995 | Gizeli | 436/527 |
| 5,517,076 | 5/1996 | Takeuchi et al. | 310/358 |
| 5,637,949 | 6/1997 | Isogai et al. | 310/330 |
| 5,698,931 | 12/1997 | Shibata et al. | 310/338 |

*Primary Examiner*—Thomas M. Dougherty
*Attorney, Agent, or Firm*—Weingarten, Schurgin, Gagnebin & Hayes LLP

[57] ABSTRACT

A dust sensing apparatus uses a transducer element oscillating at a resonant frequency to detect changes in dust concentration. The transducer is fabricated from a polymer material which oscillates when a voltage is applied. The presence of dust affects the oscillation frequency. Dampening of the frequency by the dust presence changes the electrical resistance provided by the transducer. Electronic circuitry computes the level of dust by measuring and controlling the level of the AC signal required to maintain the oscillation frequency by monitoring the resistance.

16 Claims, 2 Drawing Sheets

DUST SENSOR APPARATUS

CROSS REFERENCE TO RELATED APPLICATIONS

This application claims priority to U.S. provisional Pat. application No. 60/042,765, entitled Apparatus and Method for Sensing Dust, filed Mar. 20, 1997.

STATEMENT REGARDING FEDERALLY SPONSORED RESEARCH OR DEVELOPMENT

None

BACKGROUND OF THE INVENTION

Sensors of small, airborne particles such as dust typically incorporate a mechanical, electrical, or optical sensing mechanism from which a output, or response signal, is measured. The magnitude of this response signal is proportional to the dust quantity. Physical qualities of such dust, such as size, density, and concentration are determined from the effect on this output signal.

Known methods used to effect such a dust sensing system include optical sensors, such as that disclosed in U.S. Pat. No. 5,136,750 in which the flux received is clouded by intervening particulate matter, and mirror based systems, such as that disclosed by U.S. Pat. No. 5,412,221 which receive light reflected from a mirror onto which particles have accumulated. Other methods include mechanical and electronic stimulation of a sensing member, typically an electrostrictive or piezoelectric member, in which particulate accumulation affects the mass of the sensor.

Such devices are disclosed in U.S. Pat. No. 3,653,253, which suggests sampling the mass of an accumulating piezoelectric crystal at two successive points to approximate the particulate mass collected, and U.S. Pat. No. 3,715,911, which discloses coating a sensory member with a tacky substance to accumulate airborne particles.

Often such devices are prone to high maintenance, as cumulative particle accumulation minimizes the sensitivity, therefore mandating frequent cleaning and/or calibration to effect accurate readings. Such devices are also expensive to manufacture, requiring specialized optical or electronic components such as piezoelectric crystals, photoresistors, and photosensors. Additionally, such devices tend to require large amounts of, or precisely metered, electrical power, limiting effectiveness with regard to household AC or common battery power. Further, point based sensors such as piezoelectric crystals have a small sensitivity area, limiting effectiveness and requiring a plurality of sensors when applied to an area. It would be beneficial to utilize a sensor capable of being manufactured from a planar material in which the electronic sensing properties are uniform along the area of the sensor.

SUMMARY OF THE INVENTION

The present invention provides a dust sensing apparatus which operates by oscillating a transducer substrate located in a sensing environment and determining the dust presence from the dampening effect such dust has on the oscillation frequency. By utilizing a conductive polymer such as poly-vinylidene-fluoride, an inexpensive yet effective sensor can be developed.

Such a substrate is treated to provide conductive portions in a particular pattern. Source electrodes are then attached to the non-conductive portions, and ground electrodes connected to the conductive portions. An AC voltage applied to the source electrodes will then create a piezoelectric effect causing substrate to deform. Rapid, alternating deformations caused by the AC voltage produce oscillatory, vibrational movement. This oscillation tends toward an inherent resonant frequency depending on the placement of the electrodes and the substrate material.

As dust presence dampens the oscillation frequency, a feedback circuit increases the voltage to drive the oscillation frequency back towards resonance. An output signal from the transducer is proportional to the amount of dust accumulated on the transducer, and also provides the feedback. The constant vibration serves to shake dust off the sensor and prevents cumulative build up, allowing the transducer to restore resonant frequency when the dust presence subsides.

DETAILED DESCRIPTION OF THE INVENTION

A dust sensing transducer apparatus according to the present invention applies an AC input signal, or voltage, to a substrate which has certain dielectric properties. This substrate is treated by irradiating or layering to form certain conductive portions, and such that an electrical field is induced within the substrate when such a signal is applied. Input electrodes are positioned on the non-treated surfaces of the substrate, and ground electrodes may be attached to the treated portions, such that the electric field so induced causes oscillatory movement of the substrate. Due to the electrical properties of the substrate, the resistance between the input electrodes varies with the oscillation rate, which is dampened by dust. The level of this resistance is linearly transferable to the quantity of dust on the sensor, and hence indicates the dust present in the sensing environment.

Figure 1:
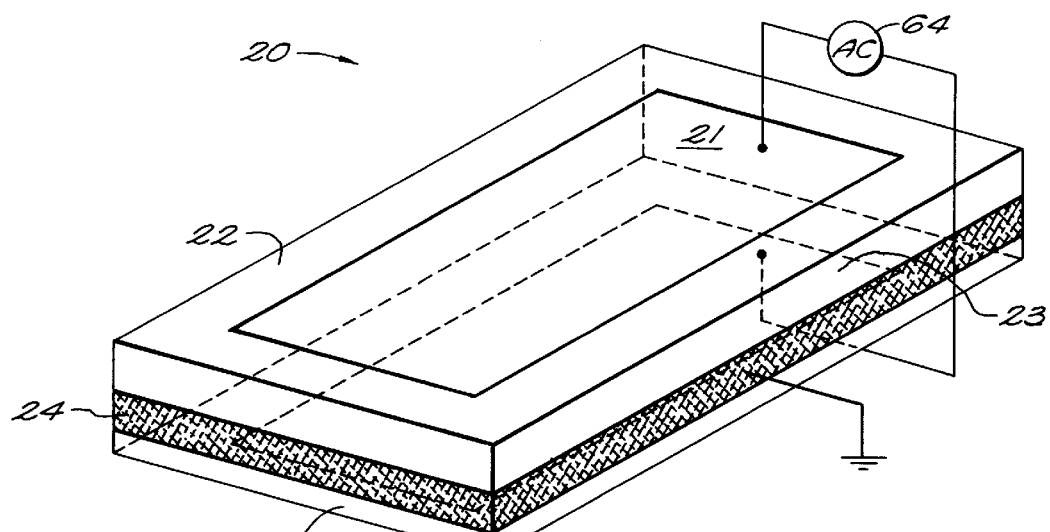
FIG. 1 is a transducer according to a first embodiment.

According to a first embodiment, a bi-morph design structure 20 is shown in FIG. 1. The bi-morph design structure 20 comprises a top layer 22 of a polymer sensor type material such as poly-vinylidene-fluoride (PVDF), a middle layer 24 of a conductive polymer, and a bottom layer 26 of a polymer sensor type material such as PVDF. The input signals 64 are applied to an electrode 21 on the top PVDF layer 22 and an electrode 23 on bottom PVDF layer 26. Electrodes 21 and 23 are of sufficient area so as to create an electric field capable of producing oscillatory movement of the substrate 20. The middle conductive layer 24 is grounded.

The bi-morph design structure 20 may also be created by irradiating the inner surfaces of the top PVDF layer 22 and the bottom PVDF layer 26 so that a resulting layer of conductive carbon remains on each inner surface. The inner surfaces may then be mated together to form a conductive carbon layer 24 between the top PVDF layer 22 and the bottom PVDF layer 26. The input signals 64 are then applied to the top PVDF layer 22 and the bottom PVDF layer 26 through electrodes 21 & 23, while the conductive carbon layer 24 is grounded.

The input signals 64 that are applied to the top PVDF layer 22 and the bottom PVDF layer 26 create an electric field which induces a piezoelectric effect in the two layers causing them to repeatedly deform and thereby cause the bi-morph design structure 20 to vibrate at its resonant frequency.

Figure 2:
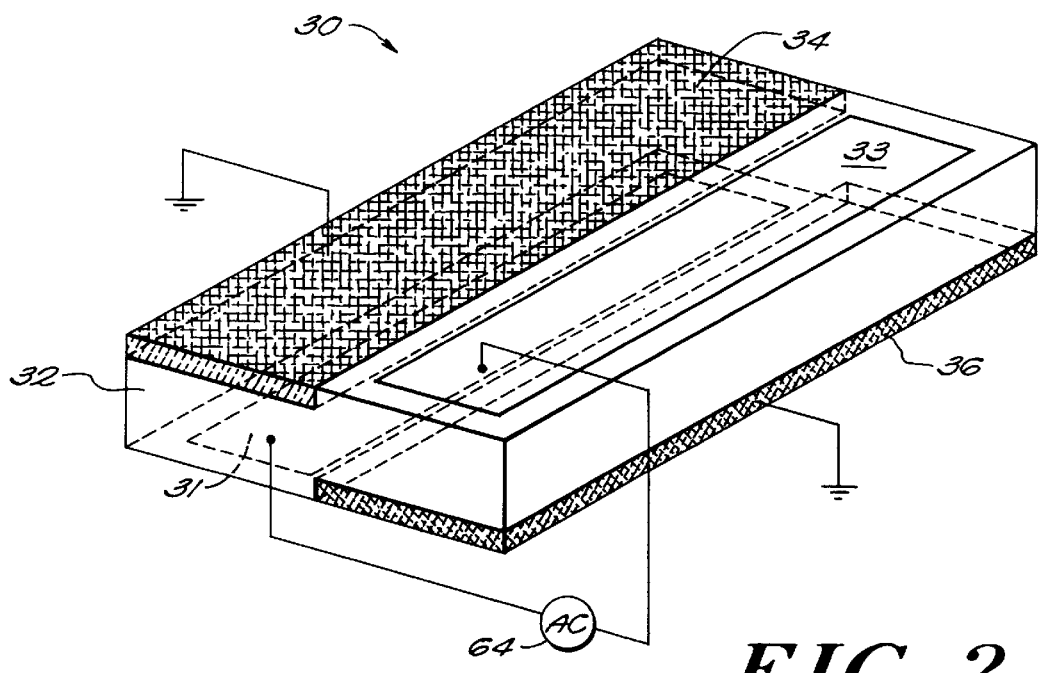
FIG. 2 is a transducer according to a second embodiment.

Referring to FIG. 2, a second embodiment comprising a half-morph design structure 30 is shown. The half-morph design structure 30 comprises a single layer 32 of PVDF of which one half of its top surface 34 and the opposing one half of its bottom surface 36 has been irradiated. The irradiated surfaces are grounded. The input signals 64 are applied to the electrodes 31 & 33 on the halves of the top and bottom surfaces of the PVDF slab 32 which have not been irradiated. The input signals 64 induce a piezoelectric effect which cause the PVDF slab 32 to repeatedly deform and thereby cause the half-morph design structure 30 to vibrate at its resonant frequency.

Figure 3:
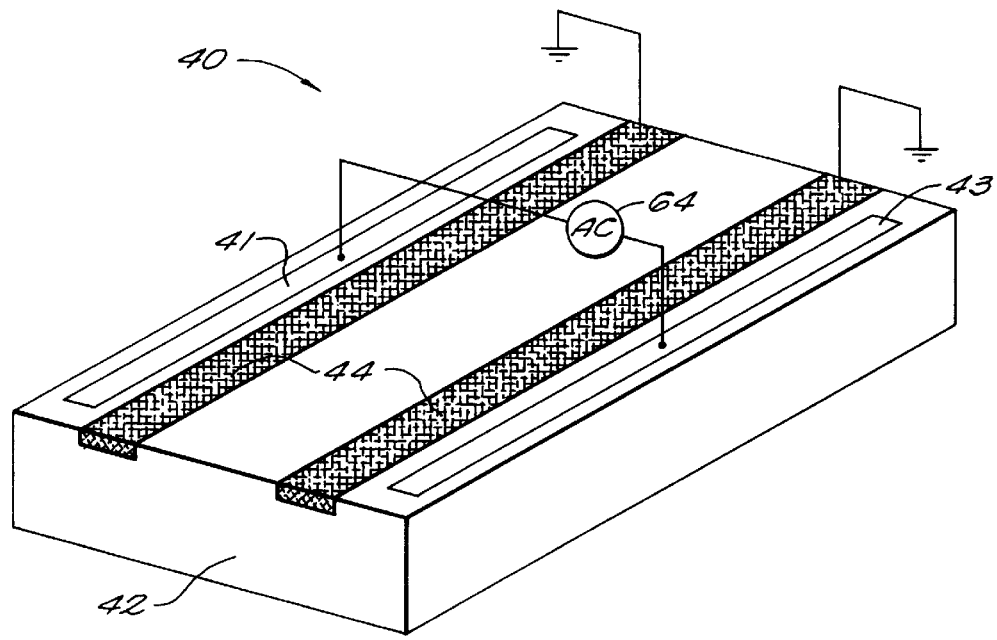
FIG. 3 is a transducer according to a third embodiment.

A third embodiment comprises a mono-morph design structure 40 as shown in FIG. 3. The mono-morph design structure 40 comprises a single layer 42 of PVDF which has had two traces 44 on its top surface irradiated. The irradiated traces are grounded. The input signals 64 are applied to the electrodes 41 & 43 on the outer areas on the top surface of the PVDF slab 42 which have not been irradiated. The input signals 64 induce a piezoelectric effect which causes the PVDF slab 42 to repeatedly deform and thereby cause the mono-morph design structure 40 to vibrate at its resonant frequency.

Although poly-vinylidene-fluoride is disclosed in the above embodiments, alternative piezoelectric crystalline materials, such as other polyvinyl compounds, a polymer matrix comprising antimony or bismuth, or other polymer matrix doped or irradiated sufficiently to sustain an electric field, could be used for fabrication of the transducer, thereby allowing for different response characteristics depending on the dielectric and resistive properties of the material chosen.

Figure 4:
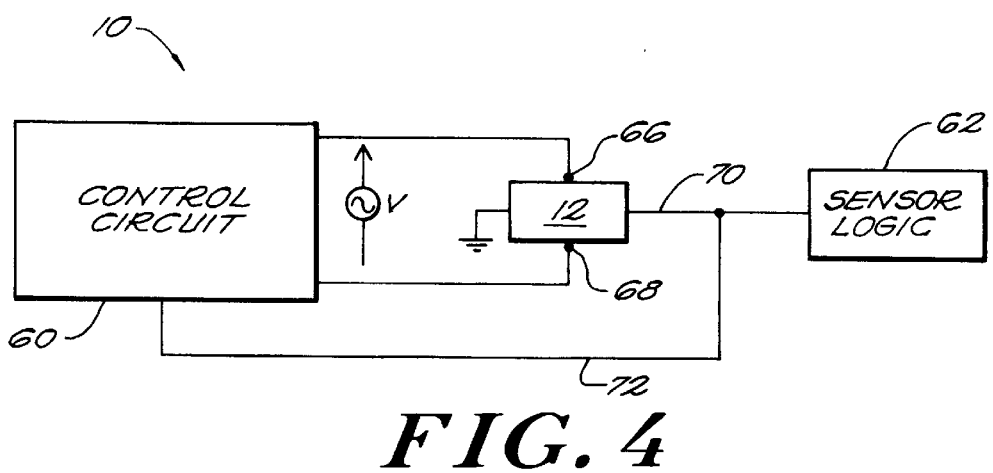
FIG. 4 is a schematic of the control and sensor logic circuit for use with the transducer.

Referring to FIG. 4, a block diagram of a dust sensor apparatus 10 comprising control circuit 60 and sensor logic circuit 62 connected to the transducer 12 is shown. The transducer 12 within this dust sensor apparatus 10 may be any of the embodiments described above.

An input voltage signal V is generated by control circuit 60 and applied to electrodes 66, 68 of transducer 12, which oscillates in response to the frequency of input voltage signal V at a resonant frequency. An output signal 70 representing the resistance of the oscillating transducer 12 provided between the electrodes 66 & 68 is received by sensor logic circuit 62 which produces an indication of the level of dust presence and concentration. Dampening of the oscillation rate in response to dust causes transducer output signal 70 to vary. An increase in the presence of dust or particles increases the dampening effect, and thus causes a proportional effect on the output signal 70, as resistance of the transducer 12 increases. The output signal 70 is also monitored by control circuit 60 via a feedback 72. In response to the output signal 70 indicating increased resistance due to dampening, control circuit 60 increases the input voltage signal V to drive the oscillation rate back to the resonant frequency. As the dust presence subsides, dust accumulated on the transducer 12 is shaken off, output signal 70 indicates decreasing resistance, and the resonant frequency is again approached. Since output signal 70 indicates decreased resistance as resonance is approached, control circuit reduces input voltage signal V accordingly to maintain resonance.

While the above embodiments describe a response to an AC voltage signal, the input signal and feedback could comprise other waveforms such as a square wave, sawtooth wave, or other extensions of a pure sine wave, and need not be a voltage source but rather any signal that produces a calibratable movement of the substrate in response to particles.

It should be understood that the invention is not limited to the particular embodiments shown and described herein, and that various changes and modifications may be made without departing from the spirit and scope of the present invention as defined by the following claims.

I claim:

1. A dust sensing apparatus comprising:
    a transducer element comprised of a substrate and having a resonant frequency, said substrate having a top surface and a bottom surface, at least one sensor portion, and at least one conductive portion; said substrate further comprising:
        a top layer, a middle layer and a bottom layer, wherein said top layer and said bottom layer are further subdivided into a plurality of segments along an axis substantially orthogonal to a plane defined by said layers;
        said at least one conductive portion further comprising at least one segment of said top layer and an opposed segment of said bottom layer; and
        said at least one sensor portion comprising the remaining segments of said top layer and said bottom layer;
    a plurality of excitation electrodes connected to said substrate, wherein said plurality of excitation electrodes comprises:
        at least one source electrode connected to said sensor portion; and
        at least one around electrode connected to said conductive portion;
        a control circuit connected to said plurality of excitation electrodes, said control circuit producing an input signal having a frequency;
        said input signal producing an electric field between said at least one sensor portion and said at least one conductive portion wherein said electric field is sufficient to produce oscillatory vibrational movement of said substrate.

2. The transducer as in claim 1 wherein said control circuit is adapted to vary said frequency in response to the rate of said oscillatory movement in response to feedback when said frequency is dampened by dust on said top surface.

3. The transducer element of claim 1
    wherein said top layer and said bottom layer comprise said at least one sensor portion; and
    said middle layer comprises said at least one conductive portion and wherein
    said oscillatory vibrational movement of said transducer is sufficient to agitate dust accumulated on said top surface.

4. The transducer element of claim 3 wherein said at least one source electrode further comprises a first source electrode connected to said top layer and a second source electrode connected to said bottom layer.

5. The transducer element of claim 1 wherein said at least one ground electrode further comprises a first ground electrode connected to one of said segments of said top layer and a second ground electrode connected to said opposed segment of said bottom layer; and
    said at least one source electrode further comprises a first source electrode connected to the sensor portion of said top layer and a second source electrode connected to said sensor portion of said bottom layer.

6. The transducer element of claim 1 wherein said at least one sensor portion comprises a piezoelectric polymer sensor material.

7. The transducer element of claim 1 wherein said at least one conductive portion comprises a piezoelectric conductive polymer.

8. The transducer element as in claim 7 wherein said conductive portion comprises an irradiated layer of said conductive polymer.

9. The transducer element of claim 8 wherein said irradiated layer is comprised of carbon.

10. The transducer element of claim 6 wherein said polymer sensor material is comprised of a polyvinyl polymer.

11. The transducer element of claim 10 wherein said polyvinyl polymer is poly-vinylidene-fluoride (PVDF).

12. A dust sensing apparatus comprising:
a transducer element comprised of a substrate and having a resonant frequency, said substrate having a top surface and a bottom surface, at least one sensor portion, and at least one conductive portion; said substrate further comprising:
   a top surface and a bottom surface, said at least one conductive portion comprising an irradiated area of said top surface and said at least one conductive portion further comprising a diagonally opposed irradiated area on said bottom surface, and
   said sensor portion comprising the non-irradiated areas of said substrate;
a plurality of excitation electrodes connected to said substrate, wherein said plurality of electrodes comprises:
   at least one source electrode connected to said sensor portion; and
   at least one ground electrode connected to said conductive portion;
   a control circuit connected to said plurality of excitation electrodes, said control circuit producing an input signal having a frequency;
   said input signal producing an electric field between said at least one sensor portion and said at least one conductive portion wherein said electric field is sufficient to produce oscillatory vibrational movement of said substrate.

13. The transducer element of claim 12 wherein said at least one ground electrode further comprises:
a first ground electrode connected to said irradiated area of said top surface; and
a second ground electrode connected to said diagonally opposed irradiated area of said bottom layer; and said at least one source electrode further comprises:
   a first source electrode connected to the non-irradiated area of said top surface; and
   a second source electrode connected to the non-irradiated area of said bottom surface.

14. A dust sensing apparatus comprising:
a transducer element comprised of a substrate and having a resonant frequency, said substrate having a top surface and a bottom surface, at least one sensor portion, and at least one conductive portion, wherein said transducer has a top surface having a perimeter defined by an outer edge and wherein said conductive portion comprises at least one trace on said top surface and said sensor portion comprises the remainder of the substrate;
a plurality of excitation electrodes connected to said substrate, wherein said plurality of electrodes further comprises:
   at least one source electrode connected to said sensor portion; and
   at least one ground electrode connected to said conductive portion;
a control circuit connected to said plurality of excitation electrodes, said control circuit producing an input signal having a frequency;
said input signal producing an electric field between said at least one sensor portion and said at least one conductive portion wherein said electric field is sufficient to produce oscillatory vibrational movement of said substrate.

15. The transducer element as in claim 14 wherein said at least one source electrode comprises:
a first source electrode connected to said sensor portion at a point more proximate to said outer edge than said at least one trace; and
a second source electrode connected to said sensor portion at an substantially opposed point more proximate to said outer edge then said at least one trace; and
said at least one ground electrode further comprises an electrode connected to each of said traces.

16. The transducer element as in claim 15 wherein said at least one trace comprises a pair of parallel trace elements extending from an edge of said top surface to an opposed edge of said top surface.

* * * * *